US00PP31973P2

(12) United States Plant Patent
Smith

(10) Patent No.: US PP31,973 P2
(45) Date of Patent: Jul. 14, 2020

(54) ***CHRYSANTHEMUM* PLANT NAMED 'CIFZ0073'**

(50) Latin Name: ***Chrysanthemum* x *morifolium***
Varietal Denomination: CIFZ0073

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,330

(22) Filed: Mar. 27, 2019

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./287, 291, 292
CPC ..... A01H 5/0255; A01H 5/02; A01H 6/1424; A01H 6/14
See application file for complete search history.

*Primary Examiner* — June Hwu
(74) *Attorney, Agent, or Firm* — Dale Skalla

(57) ABSTRACT

A new garden type *Chrysanthemum* plant named 'CIFZ0073' particularly distinguished by the medium size plant with upright to outwardly spreading and uniform mounded plant habit, a medium size (4.4 cm), dark lavender flower color and a natural season response mid-September.

1 Drawing Sheet

Figure 1:
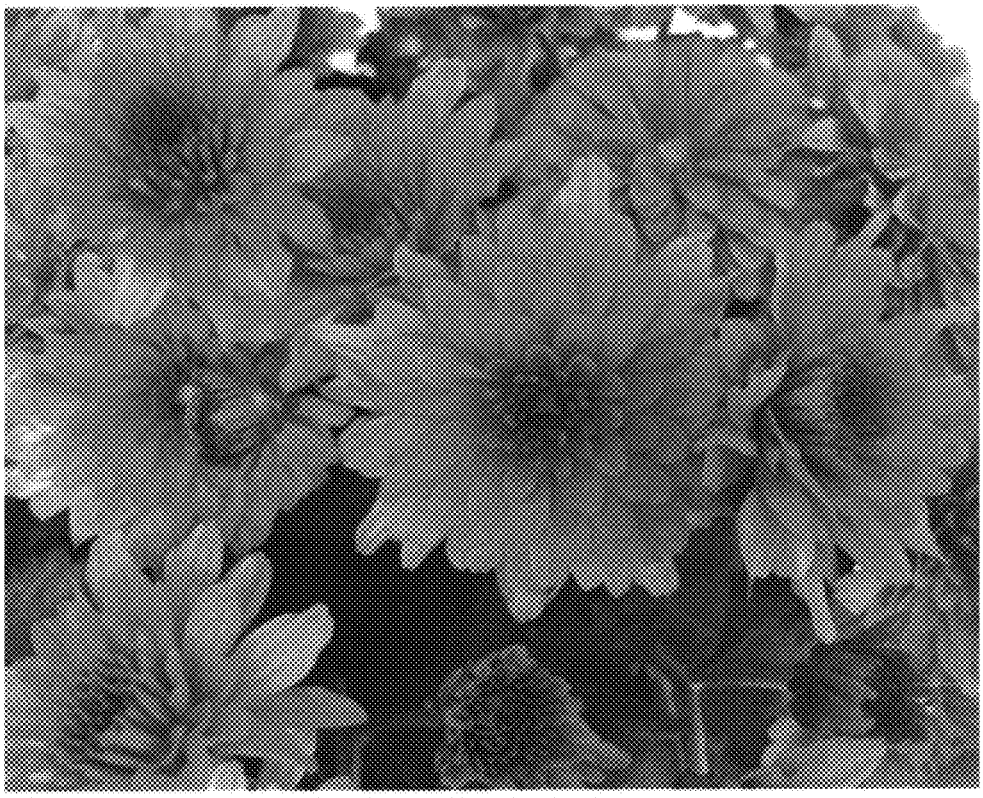

Latin name of the genus and species of the plant claimed: *Chrysanthemum* x *morifolium.*

Varietal denomination: 'CIFZ0073'.

BACKGROUND OF THE NEW PLANT

The present invention comprises a new *Chrysanthemum*, botanically known as *Chrysanthemum* x *morifolium*, and hereinafter referred to by the variety name 'CIFZ0073'.

'CIFZ0073' is a product of a planned breeding program. The new cultivar has medium size plant with upright to outwardly spreading and uniform mounded plant habit, a medium size (4.4 cm), dark lavender flower color and a natural season response mid-September.

'CIFZ0073' originated from a cross made in September 2008 in Tenjo, Columbia. Seeds were sown in June 2013 in Gilroy, Calif. and 'CIFZ0073' was selected from the resulting population on October 11 in Monroeville, N.J.

The female parent was the variety 'Zanmufive', U.S. Plant Pat. No. 19,791.

When compared to the female parent, 'CIFZ0073' has:

- a similar flower type but smaller in size and flower dark lavender (almost purple) flower color not red like 'Zanmufive'.
- a couple days slower blackcloth response and one week slower natural season response than 'Zanmufive'.
- a bit larger overall plant size and fuller and rounder plant habit than 'Zanmufive'.

The male parent was the unnamed seedling '04-M277'.

When compared to the male parent, 'CIFZ0073' has:

- a bit larger flower size with less disc florets and not as dark of a purple flower color as the male parent.
- a similar blackcloth response and similar natural season response as the male parent.
- a similar plant size and plant habit in the natural season but distinctly rounder/less upright plant habit in blackcloth than the male parent.

The first act of asexual reproduction of 'CIFZ0073' was accomplished when vegetative stem cuttings were propagated from the initial selection in January 2014 in Mebane, N.C.

BRIEF SUMMARY OF INVENTION

Horticultural examination of plants grown from cuttings of the plant initiated in January 2014 and continuing thereafter, has demonstrated that the combination of characteristics as herein disclosed for 'CIFZ0073' are firmly fixed and are retained through successive generations of asexual reproduction.

'CIFZ0073' has not been observed under all possible environmental conditions. The phenotype may vary significantly with variations in environment such as temperature, light intensity and day length.

A Plant Breeder's Right for this cultivar has not yet been applied for. 'CIFZ0073' has not been made publicly available prior to the effective filing date of this application, notwithstanding any disclosure that may have been made less than one year prior to the effective filing date of this application by the inventor or another who obtained 'CIFZ0073' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0073' with colors being as true as possible with an illustration of this type.

Figure 2:
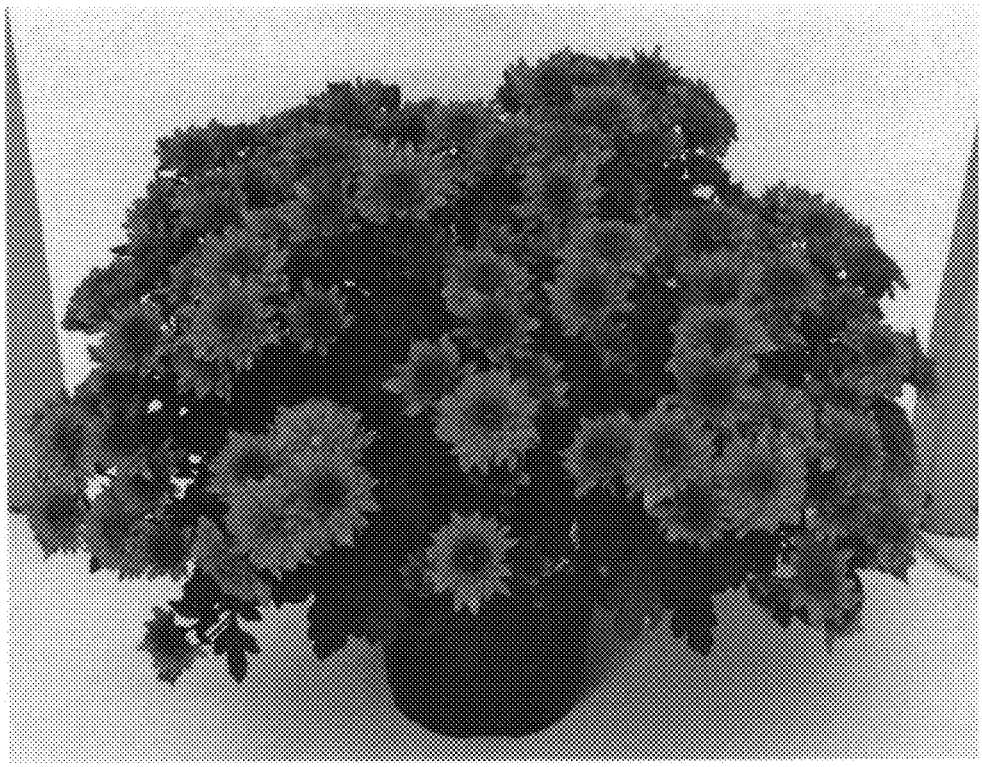

The photographic drawings show in FIG. 1 a close view of flower of the new variety and in FIG. 2 a flowering plant from an outdoor trial.

The aforementioned photographs: FIG. 1, as well as FIG. 2, were taken in August 2018 both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2018 on the plants from the aforementioned trial.

Color references are made to The Royal Horticultural Society Colour Chart (R.H.S.) 2015.

TABLE 1

DIFFERENCES BETWEEN THE NEW VARIETY 'CIFZ0073' AND 'CIFZ0003':

| | 'CIFZ0073' | 'CIFZ0003' (U.S. Plant Pat. No. 23,762) |
|---|---|---|
| Flowering response (blackcloth): | Similar | Similar |
| Flowering response (natural): | Similar | Similar |
| Plant habit and size: | Similar plant size but plant habit is a bit more upright | Similar plant size but plant habit is a bit more round |
| Plants, stems, flexibility: | Sturdier plant/less apt to split | Softer plant/more apt to split |
| Flower shape, size, color: | Similar flower form with larger flower size and similar flower color but more two-tone look with darker flower center | Similar flower form with smaller flower size and similar flower color but more uniform flower color |

TABLE 2

DIFFERENCES BETWEEN THE NEW VARIETY 'CIFZ0073' AND 'GEDI TWO PAD'

| | 'CIFZ0073' | 'Gedi Two Pad' (U.S. Plant Pat. No. 14,501) |
|---|---|---|
| Flowering response (blackcloth): | 1 week faster | 1 week slower |
| Flowering response (natural): | Similar | Similar |
| Plant habit or size: | Rounder plant habit with similar or a bit shorter plant size | More upright plant habit with similar or a bit bigger plant size |
| Flowering: | Flowers more uniformly | Flowers less uniformly |
| Flower longevity: | Similar flower size, with darker flower color and less disk florets | Similar flower size, with lighter flower color and more disk florets |

Plant:

*Form, growth and habit.*—Herbaceous garden-type, stems upright and outwardly spreading, freely branching, strong and moderately vigorous growth habit.

*Plant height* (*above soil*).—16-21 cm.

*Plant height* (*inflorescence included*).—19-24 cm.

*Plant width.*—36-40 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137B.

*Mature leaf, color, upper surface.*—RHS 137A.

*Mature leaf, color lower surface.*—RHS 137B.

*Length.*—6.1-6.2 cm.

*Width.*—4.3-5.3 cm.

*Shape.*—Ovate, with distinct lobes.

*Base shape.*—Attenuate.

*Apex shape.*—Mucronate.

*Length of terminal leaf lobe.*—Medium.

*Margin.*—5-lobed (palmate), edge dentate.

*Leaf margin number of indentation.*—Few.

*Depth indentation.*—Shallow.

*Depth of lowest lateral sinus.*—Shallow.

*Stipule.*—Not present at the leaf petiole base.

*Upper surface.*—Bifid hairs.

*Lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 138A.

*Petiole length.*—2.1-2.5 cm.

*Diameter.*—0.3-0.4 cm.

*Hairs.*—Covered with bifid hairs.

Stem:

*Quantity of main branches per plant.*—6-8.

*Color of stem.*—RHS 138B.

*Length of stem.*—6 cm.

*Diameter.*—0.7 cm.

*Length of internodes.*—1-2 cm.

*Hairs.*—Bifid hairs.

*Color of peduncle.*—RHS 138A.

*Length of peduncle.*—5.3 cm.

*Peduncle diameter.*—0.2 cm.

*Hairs.*—Bifid hairs.

Inflorescence:

*Type.*—Compositae, solitary, decorative type inflorescences borne terminally above foliage, ligulate ray and sometimes a few disc florets arranged on a capitulum.

*Quantity of short days to flowering* (*response time*).—Approximately 5 weeks.

*Natural season flowering.*—Mid-September.

*Quantity of inflorescences per plant.*—180-220.

*Lastingness of individual blooms on the plant.*—About five weeks from first color.

*Fragrance.*—Slightly spicy.

Bud (when showing color):

*Color.*—RHS 61A.

*Length.*—1.4 cm.

*Width.*—1.2 cm.

*Shape.*—Oblate.

Immature inflorescence:

*Diameter.*—3.5 cm.

*Color of ray florets, upper surface.*—RHS 70B.

*Color of ray florets, lower surface.*—RHS 70C.

Mature inflorescence:
*Diameter.*—4.1-4.5 cm.
*Depth.*—1.3-1.4 cm.
*Total diameter of disc.*—0.3 cm.
*Receptacle color.*—RHS 145A.
*Receptacle height.*—0.3 cm.
*Receptacle diameter.*—0.3 cm.
Ray florets:
*Average quantity of florets.*—Between 100-120 in several whorls.
*Color of florets, upper surface (at moment of senescence).*—RHS 77B.
*Color inner surface (at moment of senescence).*—RHS 77C.
*Length.*—2.8 cm.
*Width/diameter.*—0.5-0.6 cm.
*Length of corolla tube.*—Short.
*Shape.*—Elliptical.
*Apex shape.*—Most obtuse and dentate.
*Base shape.*—Tube.
*Margin.*—Entire, small incisions may occur at the tip.
*Type of rolling of the ray floret margin.*—Flat.
*Texture, upper surface.*—Papillate.
*Lower surface.*—Papillate.
Disc florets: 10.
*Width.*—0.1 cm.
*Length.*—0.3-0.4 cm.
*Color.*—RHS 61B at apex, RHS N144C at base.
Phyllaries:
*Quantity.*—20-22.
*Color, upper surface.*—RHS 137D.
*Color, lower surface.*—RHS 138A.
*Length.*—0.2-0.4 cm.
*Width.*—0.1-0.15 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.
Reproductive organs:
*Pistil.*—One.
*Length.*—0.4 cm.
*Style color.*—Between RHS 150A and RHS 150B.
*Style length.*—0.3 cm.
*Stigma color.*—RHS 7C.
*Stigma shape.*—Bi-parted.
*Ovary color.*—RHS 145C.
*Ovary length.*—0.15 cm.
*Ovary width.*—0.1 cm.
Androecium:
*Stamens.*—1, found on only disc florets.
*Color of filaments.*—RHS 3B.
*Length filaments.*—0.2 cm.
*Anther color.*—RHS 13B.
*Anther length.*—0.2 cm.
*Anther shape.*—Oval to club shaped.
*Color of pollen.*—RHS 13B.
*Pollen amount.*—Rather poor.
*Fertility/seed set.*—Limited fertility.
*Disease/pest resistance.*—Has not been determined to date.
*Plant hardiness zone or heat/cold resistance.*—Has not been determined to date.

What is claimed is:

1. A new and distinct variety of *Chrysanthemum* plant named 'CIFZ0073' substantially as illustrated and described herein.

* * * * *